United States Patent
Souzy et al.

(10) Patent No.: US 9,339,447 B2
(45) Date of Patent: May 17, 2016

(54) POLYMERIC AGENT FOR OBTAINING A STABLE AQUEOUS COMPOSITION COMPRISING PARTICLES IN SUSPENSION

(71) Applicant: COATEX, Genay (FR)

(72) Inventors: Renaud Souzy, Caluire et Cuire (FR); Yves Kensicher, Theize (FR); Olivier Guerret, Pern (FR)

(73) Assignee: COATEX, Genay (FR)

( * ) Notice: Subject to any disclaimer, the term of this patent is extended or adjusted under 35 U.S.C. 154(b) by 0 days.

(21) Appl. No.: 14/133,724

(22) Filed: Dec. 19, 2013

(65) Prior Publication Data

US 2014/0179590 A1    Jun. 26, 2014

Related U.S. Application Data

(60) Provisional application No. 61/740,478, filed on Dec. 21, 2012.

(30) Foreign Application Priority Data

Dec. 20, 2012  (FR) .................................... 12 62409

(51) Int. Cl.

| | | |
|---|---|---|
| *C11D 3/12* | (2006.01) |
| *C08F 220/28* | (2006.01) |
| *A61K 8/81* | (2006.01) |
| *A61K 8/04* | (2006.01) |
| *A61Q 5/02* | (2006.01) |
| *A61Q 19/10* | (2006.01) |
| *A61K 8/86* | (2006.01) |

(52) U.S. Cl.
CPC . *A61K 8/044* (2013.01); *A61K 8/86* (2013.01); *A61Q 5/02* (2013.01); *A61Q 19/10* (2013.01); *C08F 220/28* (2013.01); *A61K 2800/28* (2013.01); *A61K 2800/48* (2013.01)

(58) Field of Classification Search
CPC ...... C11D 3/12; C11D 3/3746; C11D 3/3757; C08F 220/28; A61K 8/81
USPC ............ 510/418, 475, 476; 424/70.11, 70.16, 424/78.31

See application file for complete search history.

(56) References Cited

U.S. PATENT DOCUMENTS

| | | |
|---|---|---|
| 5,294,693 A | 3/1994 | Egraz et al. |
| 5,362,415 A | 11/1994 | Egraz et al. |
| 7,790,800 B2 | 9/2010 | Suau et al. |
| 2003/0147825 A1* | 8/2003 | Chiarelli et al. ........... 424/70.11 |
| 2008/0103248 A1* | 5/2008 | Suau et al. .................... 524/548 |
| 2012/0230920 A1 | 9/2012 | Souzy et al. |
| 2014/0017184 A1 | 1/2014 | Fumagalli et al. |
| 2014/0018284 A1 | 1/2014 | Coget et al. |

FOREIGN PATENT DOCUMENTS

| | | |
|---|---|---|
| EP | 0 577 526 A1 | 1/1994 |
| FR | 2 872 815 A1 | 1/2006 |
| WO | WO 2011/117427 A2 | 9/2011 |

OTHER PUBLICATIONS

U.S. Appl. No. 14/133,735, filed Dec. 19, 2013, Souzy et al.
International Search Report issued Feb. 13, 2014 in PCT/FR2013/053175.

* cited by examiner

*Primary Examiner* — Brian P Mruk
(74) *Attorney, Agent, or Firm* — Oblon, McClelland, Maier & Neustadt, L.L.P.

(57) ABSTRACT

Agent for obtaining a stable aqueous composition comprising a polymer constituted of:
  at least one A monomer of acrylic acid and/or methacrylic acid and/or any of their salts,
  at least one B monomer of alkyl acrylate and/or methacrylate, and
  at least one C monomer corresponding to the following formula (I):

$$T\text{-}[(EO)_n(PO)_{n'}(BO)_{n''}]\text{-}Z \qquad (I)$$

in which:
  T represents one end enabling the co-polymerization of the C monomer,
  $[(EO)_n(PO)_{n'}(BO)_{n''}]$ represents a polyalkoxylated chain constituted of alkoxylated units, distributed into blocks, alternatively or statistically, chosen from among EO ethoxylated units, PO propoxylated units and BO butoxylated units, representing, independently from each other, 0 or a whole number between 1 and 150, the sum of n, -n' and n" not being null, and
  Z represents a fatty chain, linear or branched, of at least 16 carbon atoms,
  at least one crosslinked monomer D.

9 Claims, No Drawings

POLYMERIC AGENT FOR OBTAINING A STABLE AQUEOUS COMPOSITION COMPRISING PARTICLES IN SUSPENSION

REFERENCE TO PRIOR APPLICATIONS

This application claims priority to U.S. provisional application Ser. No. 61/740,478, filed Dec. 21, 2012; and to French patent application 12 62409, filed Dec. 20, 2012, both incorporated herein by reference.

This invention concerns the formulation of stable aqueous compositions comprising particles in suspension.

The problem encountered in formulating these compositions mainly lies in a homogenous distribution of particles in the composition and their stability over time, particularly during storage.

In the preparation of these compositions, this parameter is of course merely one criterion to be met among other essential ones, such as viscosity, pH, clarity, stability . . . . It is therefore necessary to achieve an optimum adjustment of all of these parameters, and this is an objective of the invention.

In the following description, reference is made to the formulation of cosmetic compositions, but the invention is not restricted to this scope of application, and extends to any other sector implementing such compositions, such as detergents.

In his article for Cosmetics & Toiletries® review, vol. 123, N. 12 Dec. 2008, "Formulating at pH 4-5: How Lower pH Benefits the Skin and Formulations", J W Wiechers expresses his surprise that, the skin's natural pH being acid, at around 4.7, most available cosmetic compositions have a higher pH, of around 6 and above. Such pH variations are not without impact on a skin that is regularly subject to them, for example in terms of the development of human cutaneous micro flora, and he highlights the benefits conferred by cosmetic formulations with a pH close to 4.7. In particular he observes increased penetration of certain active principles, as well as better preservation of same at these pH values, making it possible to limit the use of preservatives.

In addition to the problem raised by the presence of particles, the formulator of acid aqueous compositions encounters difficulties, because the continuous phase of these compositions is not stable, rapidly evolving towards a dephasing. This phenomenon is particularly visible when compositions comprise particles in suspension, which can also be dragged to the bottom or surface of the container.

Document WO 03/061615A describes cosmetic compositions formulated at a pH of between 6 and 7, used as a hair fixing agent. They contain a thickener consisting of a HASE (hydrophobically modified alkali-swellable) polymer, obtained through the polymerisation of methacrylic acid, ethyl acrylate, a hydrophobic monomer comprising a polymiserable end such as acrylic acid, an ethoxylated mid part and a hydrophobic end consisting of a linear hydrocarbonated fatty chain and a crosslinking monomer. The compositions thus formulated have a rheology such that they are sprayable, and do not flow on the hair, while drying rapidly once applied. This document mainly describes the properties of compounds, when used.

The problem that the invention seeks to resolve is the preparation of aqueous compositions, comprising a continuous limpid phase and particles in suspension distributed in the continuous phase, the pH of these compositions being less than 7, and these compositions being stable. An important effect is that, particularly during storage of such compositions, particles are kept in suspension in the continuous phase, which remains limpid. It must be possible to visualise these particles, having a technical or merely aesthetic function, and they must therefore be visible, at any moment.

Curiously, authors have observed that there is no correlation between the viscosity of a composition given by a thickener and the capacity of the latter to keep particles in suspension in the composition.

According to the invention, a polymer was discovered, for the formulation of aqueous acid compositions, in which this association acts as both a thickener and clarifier in the continuous phase, while allowing an even distribution of particles in the continuous phase, said compositions remaining stable over time, and in particular visibly stable.

The polymer according to the invention is obtained from the following monomers:

At least one anionic A monomer having a polymerizable vinylic function, and a carbonyl group, possibly in the form of salt, At least one non-ionic B monomer having a vynilic polymerizable function, At least one oxyalkylated C monomer having a vynilic polymerizable function, and a hydrophobic hydrocarbonated chain, and at least one crosslinking D monomer.

According to an embodiment, the C monomer follows this formula (I):

$$\text{T-}[(EO)_n(PO)_{n'}(BO)_{n''}]\text{-Z} \qquad (I)$$

in which:

T represents one end enabling the co-polymerization of the C monomer, $[(EO)_n(PO)_{n'}(BO)_{n''}]$ represents a polyalkoxylated chain consisting of alkoxylated units, distributed into blocks, alternatively or statistically, chosen from among EO ethoxylated units, PO propoxylated units and BO butoxylated units, n, n', n" representing, independently of each other, 0 or a whole number varying from 1 to 150, the sum of n, n' and n" not being null, and Z represents a fatty chain, linear or branched, of at least 16 carbon atoms.

Likewise, the C monomer may be represented as follows in the next formula (II): T-A-Z, in which:

T represents one end enabling the co-polymerization of the C monomer,

A represents a polymeric chain constituted of:

m units of alkylene oxide, formula —CH2CHR1O— with R1 representing an alkyl group comprising 1 to 4 carbons, for example a methyl or ethyl group and m varying from 0 to 150, p units of alkylene oxide, formula —CH2CHR2O— with R2 representing an alkyl group comprising 1 to 4 carbons, for example a methyl or ethyl group and p varying from 0 to 150, n units of ethylene oxide, with n varying from 0 to 150, or from 10, or 15,to 150, or from 10, or 15, to 100, or from 15 to 50, or from 15 to 30, In which m+n+p>0, and In which the alkylene oxide units of the formula —CH2CHR1O—, the alkylene oxide units of the formula —CH2CHR2O— and the ethylene oxide units are in blocks, alternatively or statistically;

Z represents a fatty chain, linear or branched, of at least 16 carbon atoms.

According to an embodiment of this invention, the polymer is obtained from the following monomers:

At least one A monomer of acrylic acid and/or methacrylic acid and/or any of their salts, At least one B monomer of alkyl acrylate and/or methacrylate, At least one C monomer corresponding to the following formula (I):

$$T-[(EO)_n(PO)_{n'}(BO)_{n''}]-Z \quad (I)$$

in which:

T represents one end enabling the co-polymerization of the C monomer, $[(EO)_n(PO)_{n'}(BO)_{n''}]$ represents a polyalkoxylated chain consisting of alkoxylated units, distributed into blocks, alternatively or statistically, chosen from among EO ethoxylated units, PO propoxylated units and BO butoxylated units, n, n', n" representing, independently of each other, 0 or a whole number varying from 1 to 150, the sum of n, n' and n" not being null, and Z represents a fatty chain, linear or branched, of at least 16 carbon atoms, and at least one crosslinking D monomer.

Thus, the invention concerns an agent for the obtention of a stable aqueous composition, comprising a continuous limpid phase and particles in suspension distributed in the continuous phase, and having a pH of less than 7, comprising a polymer resulting from the polymerisation of the A, B, C and D monomers above. It also concerns the aqueous and stable composition, thus prepared.

Before discussing the invention and its applications in more detail, certain terms used in the description and the claims are defined below.

A composition of the invention may comprise at least one active ingredient (or active agent) or a mixture of active ingredients, in any form whatsoever, and whatever the field of application of the composition, as indicated above. The active principle/s may be dissolved in the continuous phase of the composition, and/or in particulate form, non-soluble in the continuous phase, and constitute all or part of the particles in suspension.

By "particles to be in suspension to obtain a composition of the invention", we mean solid bodies, these bodies being plain or hollow, liquid or gassy, and being possibly characterised by different forms, textures, structures, compositions, colours and final properties. By way of example we can mention exfoliating particles (for example polyethylene particles, crushed fruit shells, pumice stones), nourishing particles (for example collagen spheres), pearlescent particles (for example titanium mica, distearate glycols) and aesthetic particles (for example air bubbles, flakes, pigments, possibly coloured). In respect of the suspension of air bubbles in the composition, particles may, in particular, have a size of the order of 1, 2 or 3 mm.

By "Alkyl" we mean a $C_mH_{2m+1}$ group, linear or branched, where m varies from 1 to 10, preferably from 1 to 6, indeed 1 to 3, or 1 to 2. Depending on how they are realised, having regard to the monomers available on the market, this is a methyl or ethyl group.

By "PO propoxylated units" and "BO butoxylated units", we mean ethoxylated units carrying, on one or other of their carbons, respectively a methyl or ethyl radical. An ethoxylated unit is a —$CH_2$—$CH_2$—O unit.

By "fatty chain" we mean an aliphatic hydrocarbonated chain of a fatty acid, linear or branched, comprising at least 16 carbon atoms, or 16 to 36 carbon atoms, or 16 to 32 carbon atoms.

According to the invention, the clarity or limpidity of a composition is measured by its transmittance. A method for determining the transmittance is described below in example 1, Materials and methods. It is expressed in a percentage, and a composition is considered as clear or limpid if it presents a transmittance of at least 40%.

In addition to the clarity it adds, the invention agent makes it possible to keep in suspension any particle present in the composition. The use of a composition thus formulated therefore does not require any mixing stage, even if the composition has been stored for several weeks, indeed several months.

The invention agent is particularly well suited to the preparation of a composition having a pH less than or equal to 5.5, or between 4 and 5. Such pH are close to the average pH value of the human skin, and it is thus of major interest in cosmetics.

The agent thus defined preferably has the following characteristics, considered alone or in combination:

The T end represents a radical containing an unsaturated polymerisable function, belonging to the group of acrylic, methacrylic, maleic, itaconic or crotonic esters. In particular, the T end may be chosen from acrylate, methacrylate, allylic, vinylic groups.

According to an embodiment, the C monomer follows this formula (III):

$$CH_2=C(R1)-COO-[(EO)_n(PO)_{n'}(BO)_{n''}]-Z$$

in which:

R1 represents H or $CH_3$, n, n', n" and Z have the same definition as in the formula (I) below.

Likewise, the C monomer follows this formula (IV):

$$CH_2=C(R1)-COO-A-Z$$

in which:

R1 represents H or $CH_3$, n, n', n", A and Z have the same definition as in the formula (II) below.

The agent according to the present invention includes one or more cross-linking monomers D). According to one embodiment, it has a single cross-linking monomer. According to another embodiment, it has two cross-linking monomers. The cross-linking monomer(s) is(are) used to prepare a copolymer in the form of a three-dimensional network.

According to the present invention, the monomer that is used is a polyunsaturated compound. This compound can have two, three or more ethylenic unsaturations.

The cross-linking monomer can have a hydrophilic, hydrophobic or amphiphilic character.

Examples of these compounds include the di(meth)acrylate compounds such as di(meth)acrylate of ethylene glycol, di(meth)acrylate of polyethylene glycol, di(meth)acrylate of triethylene glycol, di(meth)acrylate of 1,3-butylene glycol, 1,6-butylene glycol di(meth)acrylate, 1,6-hexanediol di(meth)acrylate, neopentyl glycol di(meth)acrylate, 1,9-nonanediol di(meth)acrylate, 2,2'-bis(4-(acryloxy-propyloxyphenyl)propane, 2,2'-bis(4-(acryloxydiethoxy-phenyl)propane, and zinc acrylate; the tri(meth)acrylate compounds such as tri(meth)acrylate of trimethylolpropane, tri(meth)acrylate trimethylolethane, tri(meth)acrylate pentaerythritol and tri(meth)acrylate of tetramethylolmethane; the tetra (meth)acrylate compounds such as ditrimethylolpropane tetra(meth)acrylate, tetramethylolmethane tetra(meth)acrylate, and pentaerythritol tetra(meth)acrylate; the hexa(meth)acrylate compounds such as dipentaerythritol hexa(meth)acrylate; the penta(meth)acrylate compounds such as the penta (meth)acrylate of dipentaerythritol; the allyl compounds such as allyl (meth)acrylate, diallylphthalate, diallyl itaconate, diallyl fumarate, and diallyl maleate; the polyallyl ethers of sucrose with from 2 to 8 groups per molecule, the polyallyl ethers of pentaerythritol such as pentaerythritol diallyl ether, pentaerythritol triallyl ether, and pentaerythritol tetraallyl ether; the polyallyl ethers of trimethylolpropane such as trimethylolpropane diallyl ether and trimethylolpropane triallyl ether. Other polyunsaturated compounds include divinyl glycol, divinyl benzene, divinylcyclohexyl and methylenebisacrylamide.

According to another aspect, the cross-linking monomers can be prepared by a reaction of esterification of a polyol with an unsaturated anhydride such as maleic anhydride or itaconic anhydride, or by a reaction of addition with an isocyanate such as 3-isopropenyl-dimethylbenzene isocyanate.

The following unsaturated compounds which cross-link by means of their pendant carboxyl groups can also be used: polyhaloalkanols such as 1,3-dichloroisopropanol and 1,3-dibromoisopropanol; haloepoxyalkanes such as epichlorohydrin, epibromohydrin, 2-methyl epichlorohydrin, and epiiodohydrin; polyglycidyl ethers such as 1,4-butanediol diglycidyl ether, glycerine-1,3-diglycidyl ether, ethylene glycol diglycidyl ether, propylene glycol diglycidyl ether, diethylene glycol diglycidyl ether, neopentyl glycol diglycidyl ether, polypropylene glycol diglycidyl ethers, bisphenol A-epichlorohydrin epoxy resins and mixtures.

The proportion of A, B, C and D monomers varies from 10-50%, from 40-80%, from 0.05-15%, and from 0.05 to 10%, respectively, by weight compared with the total weight of the polymer. In one embodiment, the proportion of A, B, C and D monomers varies from 30-45%, from 50-65%, from 0.05 to 12%, and from 1.5 to 5%, respectively, by weight compared with the total weight of the polymer.

Polymers are prepared according to procedures known to a skilled man in the art. More precisely, they are obtained by procedures known as conventional radical copolymerization in solution, in direct or inverse emulsion in bulk, in suspension or precipitation in the appropriate solvents, in the presence of known initiators and transfer agents, or by controlled radical polymerization procedures, such as the method called Reversible Addition Fragmentation Transfer (RAFT), the method called Atom Transfer Radical Polymerization (ATRP), the method called Nitroxide Mediated Polymerization (NMP), or the method called Cobaloxime Mediated Free Radical Polymerization. The polymerization should preferably be realised in emulsion.

The invention also concerns an aqueous cosmetic composition, comprising a continuous phase and particles in suspension in the continuous phase, said continuous phase and/or said particles comprising and/or consisting of an active cosmetic principle, and having a pH lower than 6, advantageously comprised between 4 and 5, said composition comprising an agent as defined above. In respect of active principle/s, they may comprise a cleaning base for the body and/or the hair. In such a composition, the proportion of the invention agent can vary from 0.1 to 20%, or from 5 to 15% by weight compared with the total weight of the composition.

The invention further concerns the use for the preparation of a stable aqueous composition, comprising a continuous limpid phase and particles in suspension distributed in the continuous phase, and having a pH lower than 7, of a polymer as defined above.

This invention is now illustrated, non-exhaustively, by the following examples.

EXAMPLE 1

Materials and Methods

The advantages of the invention can be shown by measuring the properties of the invention compositions, compared with those of compositions comprising a thickening agent known to a skilled man in the art.

Organoleptic properties of a Composition:

The organoleptic properties of different cosmetic compositions such as shower gel/shampoo, are tested, formulated and stored in a heat chamber (45° C.) for 3 months. The evaluation is carried out at room temperature. The following criteria are taken into account: Opacity (variation from limpid to opaque, indeed intense white), Texture (unctuous, presence of lumps, grains . . . ), Odour (whether or not there is an odour), Colour (variation in homogeneity), and Surface (smooth or not smooth).

Clarity or Limpidity of a Composition:

Limpidity is measured by measuring transmittance in the following way:

Measurements are taken on a UV Genesys Spectrometer 10 UV™ (Cole parmer), equipped with Rotilabo-Einmal Kuvetten PS, 4.5 mL vessels. In practical terms, the device is heated 10 minutes before use. Firstly an initial measurement is carried out using a vessel filled with 3.8 mL of bipermuted water (the "blank"). The measurement is then taken with a vessel filled with 3.8 mL of the solution of cosmetic composition to be tested. The transmittance is then measured with a wave length of 500 nm.

The higher the transmittance value, expressed in %, the more limpid the cosmetic composition is. As stated above, the composition is considered to be limpid at a transmittance value of at least 40%.

Visco-Elasticity of a Composition:

Visco-elasticity measurements of different formulations are carried out with the help of a Haake-RheoStress RS 150 type rheometer. The variation of the dephasing angle ($\delta$, in °), depending on the constraint $\tau$ (scanning from 0 to 800 Pa) is measured at 25° C., thanks to the cone-plate module (1°). The flow limit value (YV, Pa or Dyn/cm$^2$) is deduced from these measurements.

Stability of a Composition:

A stability test of different sun protection formulae is carried out:

at t=1 month—Sample stored at +4° C.

at t=3 months—Sample stored at +45° C.

Potential instabilities such as dephasing, creaming, bleeding, releasing, deposit/sedimentation are observed.

Viscosity of a Composition:

The viscosity of said formulae is measured using a Brookfield viscometer, RVT model. Before measuring viscosity, each formulation is left to rest 24 hours at 25° C. The spindle must be centered on the flask's opening.

Then, viscosity is measured at 6 rpm (rotations per minute) using the appropriate modulus.

The viscometer is left to rotate until the viscosity is stable.

EXAMPLE 2

Ultra-Soft Exfoliating Shampoo

This example illustrates the use of agents according to the invention in ultra-soft shampoo type cosmetic formulation, and aims to show the rheological (suspension and viscosity) and organoleptic properties provided according to the invention.

Thus, from a shampoo formulation based on anionic and zwitterionic surfactants, the composition of which is shown in table 1, the aim is to verify in this formulation the limpidity, viscosity and suspension as affected by different rheology modifiers, including those of prior art and those according to the invention. The values mentioned in the last column of the table indicate the masses in grams.

TABLE 1

| | |
|---|---|
| 1-DI water | QSF 100 |
| 2-Texapon NSO UP, 28 (Cognis) | 32.14 |
| 3-Dehyton PK 45 (Cognis) | 6.67 |
| 4-Rheology Modifier | Tested polymer |
| 5-Sodium Hydroxide | Qs pH = 6.0 or 7.0 ± 0.1 |
| 6-Lactic Acid | Qs pH 5.0 ± 0.1 |
| 7-Potassium sorbate (Nutrinova) | 0.40 |
| 8-Strawberry Fragrance (Hyteck) | 0.50 |
| 9-Exfoson Quin 300 red, Exfoliating particles (Soniam) | 2.00 |

Formulation Preparation Protocol:
The bipermuted water (1) is placed in a beaker, and then the different ingredients (2) and (3) are added under stirring.
After total homogeneization, the rheology modifier (4) is very gently added under stirring.
The pH is measured, which is then adjusted to 5.0±0.1 or 6.0±0.1 or 7.0±0.1 with the ingredients (5) or (6).
After verifying the pH, the preserver (7) and the perfume (8) are mixed, with moderate stirring, into the shampoo formulation.
The exfoliating quinoa particles (9) are then dispersed, by stirring.
Table 2 summarises all the rheology modifiers that have been used as an ingredient (4) within the framework of tests of this example 2. Note that their quantity is expressed by weight percentage compared with the total weight of the composition. By way of example, if the weight percentage is equal to 5%, we add 5 g of (4) for a formulation of 100 g of finished product.

In table 2:
REF: Reference/PA: Prior Art/INV: Invention/OI: Outside Invention/NA: Not applicable.
Z: Number of carbon atoms of the fatty chain, linear or branched.
EDMA: Ethylene Glycol Dimethacrylate
TMP-TMA: Trimethylolpropane Trimethacrylate
NDMA: 1,9-nonanediol di(meth)acrylate
NPGDE: neopentyl glycol diglycidyl ether Test 1-1:
The ingredient (4) is an inorganic salt: Sodium chloride.
Test 1-2:
The ingredient (4) is a crosslinked polymer additive, of the crosslinked polyacrylate type, Carbopol® ETD (Lubrizol)
Test 1-3:
The ingredient (4) is an Aqua SF1 type additive (Lubrizol).
Test 1-4:
The ingredient (4) here is an ethyl acrylate/methacrylic acid crosslinked ASE polymer additive.
Tests 1-5 to 1-14:
The ingredients (4) are polymers resulting from the polymerisation of A, B, C, D monomers, defined in table 2; only tests 1-5 to 1-12 correspond to the use of an agent of the invention.
The application results are presented in Tables 3 and 4.

TABLE 2

| | | | Ingredient (4) | | | | | | | | |
|---|---|---|---|---|---|---|---|---|---|---|---|
| | Physical state | Physical state | | Rheological Additive Composition (weight %) | | | | | | | |
| | Solid at 100% of | Aqueous solution % | | | Methacrylic | | | | Characteristics of Monomer C: | | |
| Test | active matter | of Active Matter | Ingredient (4) (%) | Ethyl Acrylate B | Acid A | Monomer D | Monomer C | T | Carbon Z | n' | n | Ramification Z |
| 1-1 (REF) | Yes | NA | 3.0 | NA | NA | NA | NA | NA | NA | NA | NA | NA |
| 1-2 (PA) | Yes | NA | 3.0 | NA | NA | NA | NA | NA | NA | NA | NA | NA |
| 1-3 (PA) | No | 30.0 | 10.0 | NA | NA | NA | NA | NA | NA | NA | NA | NA |
| 1-4 (PA) | No | 30.0 | 10.0 | 53.5 | 43.1 | 3.4 (EDMA) | 0 | NA | NA | NA | NA | NA |
| 1-5 (INV) | No | 30.0 | 10.0 | 60.4 | 34.6 | 4.5 (EDMA) | 0.5 | Methacrylate | 32 | 0 | 25 | branched |
| 1-6 (INV) | No | 30.0 | 8.5 | 58.5 | 39.05 | 0.45 (NDMA) | 2.0 | Methacrylate | 32 | 0 | 25 | branched |
| 1-7 (INV) | No | 30.0 | 10.0 | 59.6 | 34.1 | 4.4 (EDMA) | 1.9 | Methacrylate | 16 | 0 | 25 | branched |
| 1-8 (INV) | No | 30.0 | 6.6 | 52.8 | 35.5 | 1.6 (EDMA) | 10.1 | Methacrylate | 20 | 0 | 25 | branched |
| 1-9 (INV) | No | 30.0 | 6.6 | 52.8 | 35.5 | 1.6 (EDMA) | 10.1 | Methacrylate | 20 | 0 | 36 | branched |
| 1-10 (INV) | No | 30.0 | 7.0 | 57.9 | 37.8 | 0.8 (NPGDE) | 3.5 | Methacrylate | 20 | 0 | 25 | branched |
| 1-11 (INV) | No | 30.0 | 10.0 | 59.8 | 34.3 | 4.5 (EDMA) | 1.4 | Methacrylate | 16 | 0 | 25 | linear |
| 1-12 (INV) | No | 30.0 | 10.0 | 52.8 | 42.1 | 2.4 (EDMA) | 2.7 | Methacrylate | 22 | 0 | 25 | linear |
| 1-13 (OI) | No | 30.0 | 10.0 | 52.6 | 37.1 | 5.1 (EDMA) | 5.2 | Methacrylate | 12 | 0 | 23 | linear |
| 1-14 (OI) | No | 30.0 | 10.0 | 52.6 | 37.1 | 5.1 (TMP-TMA) | 5.2 | Methacrylate | 12 | 0 | 23 | linear |

TABLE 3

| | | | | pH 5 | | pH 6 | | pH 7 | |
|---|---|---|---|---|---|---|---|---|---|
| Test | Viscosity pH 5 | Viscosity pH 6 | Viscosity pH 7 | Transmittance (500 nm) | YV (dyn/cm$^2$) | Transmittance (500 nm) | YV (dyn/cm$^2$) | Transmittance (500 nm) | YV (dyn/cm$^2$) |
| 1-1 | 26900 | 25200 | 17800 | 98.4% | 0 | 98.4% | 0 | 98.6% | 0 |
| 1-2 | 6880 | 9870 | 11700 | 0.5% | 3 | 0.3% | 6 | 0.3% | 8 |
| 1-3 | 5600 | 15220 | 12750 | 5.3% | 35 | 47% | 40 | 90% | 20 |
| 1-4 | 17640 | 18420 | 2075 | 20.4% | 40 | 68.2% | 50 | 39.7% | 4 |
| 1-5 | 4320 | 26600 | 9340 | 57.5% | 20 | 81.5% | 80 | 93.2% | 30 |

TABLE 3-continued

| Test | Viscosity pH 5 | Viscosity pH 6 | Viscosity pH 7 | pH 5 Transmittance (500 nm) | pH 5 YV (dyn/cm$^2$) | pH 6 Transmittance (500 nm) | pH 6 YV (dyn/cm$^2$) | pH 7 Transmittance (500 nm) | pH 7 YV (dyn/cm$^2$) |
|---|---|---|---|---|---|---|---|---|---|
| 1-6 | 3500 | 15000 | 21500 | 63.7% | 21 | 75.5% | 29 | 92.8% | 37 |
| 1-7 | 4030 | 25790 | 25600 | 56.8% | 20 | 77.2% | 70 | 99.2% | 60 |
| 1-8 | 3800 | 9950 | 32820 | 94.9% | 10 | 95.3% | 15 | 95.8% | 25 |
| 1-9 | 5100 | 17200 | 18430 | 91.3% | 10 | 93.4% | 20 | 94.4% | 25 |
| 1-10 | 4150 | 12600 | 15450 | 59.5% | 18 | 70.1% | 22 | 92.1% | 31 |
| 1-11 | 4630 | 27800 | 22200 | 44.1% | 15 | 86.1% | 70 | 97.2% | 40 |
| 1-12 | 33100 | 43200 | 36400 | 45.5% | 20 | 72.4% | 50 | 78.9% | 40 |
| 1-13 | 7980 | 9580 | 15420 | 5.3% | 21 | 24% | 79 | 95% | 25 |
| 1-14 | 5430 | 11600 | 14950 | 10.4% | 30 | 25.4% | 35 | 97.3% | 20 |

Viscosity: Brookfield 6 rpm (cPs) $T_{24}$

TABLE 4

| Test n. | pH | Organoleptic Properties at t = 1 month | Stability at t = 1 month Sample stored at +4° C. | Stability at t = 3 months Sample stored at +45° C. |
|---|---|---|---|---|
| 1-1 | 5 | Spread: Good cover<br>Texture: Unctuous<br>Odour: Odour free<br>Aspect: limpid<br>Surface: smooth | Complete sedimentation of particles | Complete sedimentation of particles |
| 1-2 | 5 | Spread: Good cover<br>Texture: Unctuous<br>Odour: Odour free<br>Aspect: opaque<br>Surface: smooth | Stable | Slight deposit |
| 1-7 | 5 | Spread: Good cover<br>Texture: Unctuous<br>Odour: Odour free<br>Aspect: limpid<br>Surface: smooth | Stable | Stable |

Table 3 above perfectly illustrates the superiority of polymers according to the invention compared with prior art.

In fact, test 1-1 leads to limpid formulae with a low pH. On the other hand, the exfoliating particles are not stabilised. Tests of prior art are no more conclusive because in this range of pH the formulae are opaque.

At the same time, accelerated stability tests (Table 4) at t=1 month (+4° C.) and at t=3 months (+45° C.) carried out on a formulation including the polymer of test 1-3 (prior art), and at the same time on a formulation including the polymer of test 1-6 (invention) show a clear difference in the stability of particles. The stability of particles is better for formulae incorporating the additives of the invention.

EXAMPLE 3

Sulphate-Free Exfoliating Shower Gel

This example concerns the implementation of a polymer according to the invention in an exfoliating shower gel formulation which is characterised by the use of a "Sulphate-free" co-surfactant incorporating the following ingredients (figures in the last column indicate the weight percentages compared with the total weight of the composition):

TABLE 5

| 1-DI water | QSF 100 |
| 2-Steol ® CS 230 (Stepan) | 15.40 |
| 3-Protelan AGL (Z&S) | 2.50 |
| 4-Rheology Modifier | Tested polymer |
| 5-Sodium Hydroxide | Qs pH 6.0 ± 0.1 |
| 6-Lactic Acid | Qs pH 6.0 ± 0.1 |
| 7-Geogard 221 (Lonza) | 0.60 |
| 8-Spectrabead 5025 (Micropowder Inc) | 1.00 |
| 9-Floratech Pumice | 1.00 |
| 10-Lemon Fragrance (Fruitaflor Int) | 0.40 |

Formulation preparation protocol:
  The bipermuted water (1) is placed in a beaker, and then the different ingredients (2) and (3) are added under stirring.
  After total homogeneization, the rheology modifier (4) is very gently added under stirring.
  The pH is measured, which is then adjusted to 6.0±0.1 with the ingredients (5) or (6).
  After verifying the pH, the preserver (7) and the perfume (10) are mixed, with moderate stirring, into the shampoo formula.
  The exfoliating particles (8) and (9) are then dispersed, under stirring.

TABLE 6

| | | | Ingredient (4) | | | | | | | | |
|---|---|---|---|---|---|---|---|---|---|---|---|
| | Physical state | Physical state Aqueous | | Rheological Additive Composition (weight %) | | | | | | | |
| Test | Solid at 100% of active matter | solution % of Active Matter or powder | Ingredient (4) (%) | Ethyl Acrylate B | Methacrylic Acid A | Monomer D | Monomer C | T | Characteristics of Monomer C Z | n' | n | Ramification Z |
| 2-1 (REF) | Yes | NA | 3.0* | NA | NA | NA | NA | NA | NA | NA | NA | NA |
| 2-2 (PA) | No | 30.0 | 10.0** | NA | NA | NA | NA | NA | NA | NA | NA | NA |
| 2-3 (INV) | No | 30.0 | 10.0 | 60.4 | 34.6 | 4.5 (EDMA) | 0.5 | Methacrylate | 32 | 0 | 25 | branched |

TABLE 6-continued

| | | | Ingredient (4) | | | | | | | | | |
|---|---|---|---|---|---|---|---|---|---|---|---|---|
| | Physical state | Physical state Aqueous | | Rheological Additive Composition (weight %) | | | | | | | | |
| | Solid at 100% of | solution % of Active | | Ethyl | Meth-acrylic | | | | Characteristics of Monomer C | | | |
| Test | active matter | Matter or powder | Ingredient (4) (%) | Acrylate B | Acid A | Monomer D | Monomer C | T | Z | n' | n | Ramifi-cation Z |
| 2-4 (INV) | No | 30.0 | 8.5 | 58.5 | 39.05 | 0.45 (NDMA) | 2.0 | Methacrylate | 32 | 0 | 25 | branched |
| 2-5 (INV) | No | 30.0 | 10.0 | 59.6 | 34.1 | 4.4 (EDMA) | 1.9 | Methacrylate | 16 | 0 | 25 | branched |

REF: Reference/PA: Prior Art/INV: Invention/OI: Outside Invention/NA: Not applicable
Test 2-1: The ingredient (4) here is an inorganic salt: Sodium chloride
Test 2-2: The ingredient (4) here is a crosslinked polymer additive of the copolymer acrylates type, as defined in this invention

TABLE 7

| | pH 6 | | |
|---|---|---|---|
| Tests | Viscosity $T_{24}$ | Transmittance (500 nm) | YV (dyn/cm$^2$) |
| 2-1 | 10 250 | 98.4% | No suspension |
| 2-2 | 8 430 | 49.1% | 40 |
| 2-3 | 8 350 | 90.8% | 40 |
| 2-4 | 8 075 | 87.6% | 34 |
| 2-5 | 8 180 | 88.2% | 30 |

Table 7 above perfectly illustrates the superiority of polymers according to the invention compared with polymers in prior art. The value of the transmittance being clearly higher for tests illustrating the invention. And this while bringing about the desired suspensivant performances.

The invention claimed is:

1. An aqueous composition, comprising a polymer comprising, based on the total weight of the polymer, in polymerized form:
   from 10 to 50 wt. % of monomer(s) A, which is methacrylic acid or a salt thereof,
   from 50 to 65 wt. % of monomer B, which is an ethyl acrylate, and
   from 0.05 to 12 wt. % of monomer(s) C selected from monomers of formula (I):

   (I)

in which:
   T is a methacrylate,
   $[(EO)_n(PO)_{n'}(BO)_{n''}]$ is a polyalkoxylated chain of ethoxylated units EO, propoxylated units PO and butoxylated units BO, with n ranging from 15 to 30, n' and n" each representing 0, and
   Z represents a branched fatty chain of at least 16 carbon atoms, and
   from 0.05 to 1.5 wt. % cross linking monomer D having three ethylenic unsaturations.

2. The composition according to claim 1, wherein said composition has a pH less than or equal to 7.

3. The composition according to claim 1, wherein said composition has a pH less than or equal to 5.5.

4. The composition according to claim 1, wherein Z represents a branched fatty chain of 16 to 32 carbon atoms.

5. The composition according to claim 1, comprising from 0.1 to 20 wt. % of said polymer based on the total weight of the composition.

6. The composition according to claim 1, wherein said composition is a cosmetic composition.

7. A method for preparing the stable aqueous composition of claim 1, said method comprising combining water, particles, and said polymer.

8. The method according to claim 7, wherein Z represents a branched fatty chain of 16 to 32 carbon atoms.

9. A cosmetic composition, comprising water, a continuous phase, particles in suspension in the continuous phase, and a polymer comprising, based on the total weight of the polymer, in polymerized form:
   from 10 to 50 wt. % of monomer(s) A, which is methacrylic acid or a salt thereof,
   from 50 to 65 wt. % of monomer B, which is an ethyl acrylate, and
   from 0.05 to 12 wt. % of monomer(s) C selected from monomers of formula (I):

   (I)

in which:
   T is a methacrylate,
   $[(EO)_n(PO)_{n'}(BO)_{n''}]$ is a polyalkoxylated chain of ethoxylated units EO, propoxylated units PO and butoxylated units BO, with n ranging from 15 to 30, n' and n" each representing 0, and
   Z represents a branched fatty chain of at least 16 carbon atoms, and
   from 0.05 to 1.5 wt. % cross linking monomer D having three ethylenic unsaturations.

* * * * *